US006646165B2

(12) United States Patent
Hiyama et al.

(10) Patent No.: US 6,646,165 B2
(45) Date of Patent: Nov. 11, 2003

(54) PROCESS FOR PRODUCING BISHALOPHENYL DISULFIDE

(75) Inventors: Takehiro Hiyama, Hyogo (JP); Hitoshi Karino, Hyogo (JP); Shinji Nii, Hyogo (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days.

(21) Appl. No.: 10/239,437

(22) PCT Filed: Apr. 16, 2001

(86) PCT No.: PCT/JP01/03211
§ 371 (c)(1),
(2), (4) Date: Sep. 20, 2002

(87) PCT Pub. No.: WO01/81299
PCT Pub. Date: Nov. 1, 2001

(65) Prior Publication Data
US 2003/0060665 A1 Mar. 27, 2003

(30) Foreign Application Priority Data
Apr. 26, 2000 (JP) ........................................ 2000-125375

(51) Int. Cl.$^7$ ...................... C07C 321/12; C07C 323/07
(52) U.S. Cl. ........................................... 568/26; 568/65
(58) Field of Search ............................... 568/21, 26, 24, 568/25, 61, 65

(56) References Cited

U.S. PATENT DOCUMENTS

| | | | | | |
|---|---|---|---|---|---|
| 3,461,168 | A | * | 8/1969 | Laufer | 568/24 |
| 4,006,186 | A | * | 2/1977 | Engels et al. | 564/440 |
| 4,039,586 | A | * | 8/1977 | Shasha et al. | 530/408 |
| 5,750,763 | A | * | 5/1998 | Sugiyama et al. | 560/17 |
| 5,998,670 | A | * | 12/1999 | Tang et al. | 568/26 |
| 6,235,941 | B1 | * | 5/2001 | Cheng et al. | 568/26 |

OTHER PUBLICATIONS

CA:60:16241 abs of J Org Chem. by Yiannios et al 28(11) pp 3246–8, 1963.*
CA:93:204191 abs of J Org. Chem. by Testaferri et al 45(22) pp 4376–80, 1980.*
CA:126:250983 abs of JP 0904636, Feb. 1997.*
CA:128:48010 abs of Journal of Chem. Soc. Perkin Trans. 2: Physical Org. Chem, by Takeuchi et al (110 pp. 2301–2306, 1997.*

* cited by examiner

*Primary Examiner*—Jean F. Vollano
(74) *Attorney, Agent, or Firm*—Knobbe, Martens, Olson & Bear LLP

(57) ABSTRACT

This invention is directed to a process for producing a bishalophenyl disulfide, chracterized by reacting a halothiophenol with an alkali metal hydroxide to obtain an alkali metal halothiophenolate and subsequently converting the halothiophenolate into a disulfide with an oxidizing agent in the presence of a mineral acid. By the process, a bishalophenyl disulfide having a high purity can be industrially produced in high yield.

7 Claims, No Drawings

PROCESS FOR PRODUCING BISHALOPHENYL DISULFIDE

This application is a 371 of PCT JP01/03211, filed Apr. 16, 2001, now WO01/81299.

FIELD OF THE INVENTION

The present invention relates to a process for producing a bishalophenyl disulfide. The bishalophenyl disulfide is a useful compound which is used for a wide variety of applications including medicine, agricultural chemicals, functional materials and the like.

BACKGROUND ART

Conventional processes for producing a bishalophenyl disulfide include a process wherein a halothiophenol is oxidized. The halothiophenol can be prepared, for example, by converting a halobenzene into a methylthiohalobenzene with an alkali metal methylmercaptide, and making the same into a halomethylthiohalobenzene with a halogenating agent, followed by hydrolysis according to the process disclosed in Japanese Unexamined Patent Publication No. 40636/1997.

When the halothiophenol used as the raw material is free of impurities in production of a bishalophenyl disulfide, a bishalophenyl disulfide having a high purity can be obtained by usual oxidation. However, when a disulfide is produced by oxidizing a low-purity halothiophenol containing impurities such as halobenzene, halomethylthiohalobenzene, bishalothiophenylmethane or the like, a problem is posed in that it is difficult to separate the disulfide as the contemplated product from the oxide derived from impurities, and a bishalophenyl disulfide can not be obtained with a high purity in a high yield.

DISCLOSURE OF THE INVENTION

A principal object of the invention is to provide a process for industrially producing a bishalophenyl disulfide having a high purity in a high yield even when a low-purity halothiophenol is used as the raw material.

The present inventors conducted extensive research to achieve the foregoing object, and found that an alkali metal halothiophenolate produced by reaction of a halothiophenol with an alkali metal hydroxide is easily dissolved in an aqueous solution of alkali metal hydroxide and that the impurities in the halothiophenol are insoluble in water. Based on this novel finding, the present invention was completed.

The present invention provides the following processes for producing a bishalophenyl disulfide and the following process for producing a halothiophenol used as the raw material.

1. A process for producing a bishalophenyl disulfide represented by the formula (3)

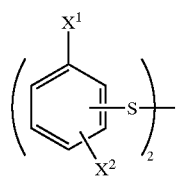
(3)

wherein $X^1$ is a halogen atom and $X^2$ is a halogen atom or a hydrogen atom, the process comprising the steps of reacting a halothiophenol represented by the formula (1)

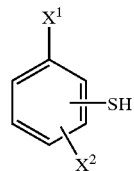
(1)

wherein $X^1$ and $X^2$ are as defined above with an alkali metal hydroxide to obtain an alkali metal halothiophenolate represented by the formula (2)

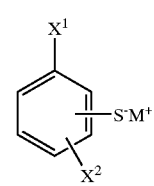
(2)

wherein $X^1$ and $X^2$ are as defined above, and M is an alkali metal atom and subsequently converting the alkali metal halothiophenolate into a disulfide with an oxidizing agent in the presence of a mineral acid.

2. The process according to item 1, wherein the alkali metal hydroxide is potassium hydroxide or sodium hydroxide.

3. The process according to item 1, wherein the mineral acid is hydrochloric acid.

4. The process according to item 1, wherein the oxidizing agent is hydrogen peroxide.

5. The process according to item 1, wherein the halothiophenol is 2-chlorothiophenol, 3-chlorothiophenol, 4-chlorothiophenol, 2-bromothiophenol, 3-bromothiophenol, 4-bromothiophenol, 2,3-dichlorothiophenol, 2,4-dichlorothiophenol, 2,5-dichlorothiophenol, 3,4-dichlorothiophenol, 3,5-dichlorothiophenol, 2,3-dibromothiophenol, 2,4-dibromothiophenol, 2,5-dibromothiophenol, 3,4-dibromothiophenol or 3,5-dibromothiophenol.

6. The process according to item 1, wherein the halothiophenol of the formula (1) is prepared by the steps of reacting a halobenzene represented by the formula (4)

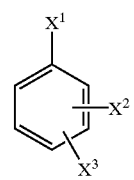
(4)

wherein $X^1$ and $X^3$ are each a halogen atom and $X^2$ is a halogen atom or a hydrogen atom, with sodium thiomethoxide in the presence of a quaternary phosphonium salt to obtain a methylthiohalobenzene represented by the formula (5)

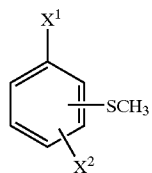
(5)

wherein $X^1$ and $X^2$ are as defined above, chlorinating the obtained methylthiohalobenzene with chlorine to obtain a chloromethylthiohalobenzene represented by the formula (6)

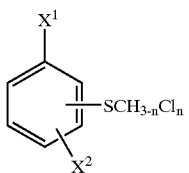
(6)

wherein $X^1$ and $X^2$ are as defined above, and n is an integer of 1 to 3, and hydrolyzing the obtained chloromethylthiohalobenzene in the presence of a lower alcohol or a base.

7. A process for producing a halothiophenol represented by the formula (1)

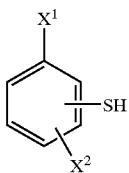
(1)

wherein $X^1$ is a halogen atom and $X^2$ is a halogen atom or a hydrogen atom, the process comprising the steps of reacting a halobenzene represented by the formula (4)

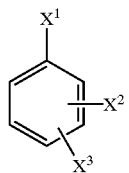
(4)

wherein $X^1$ and $X^2$ are as defined above, and $X^3$ is a halogen atom, with sodium thiomethoxide in the presence of a quaternary phosphonium salt to obtain a methylthiohalobenzene represented by the formula (5)

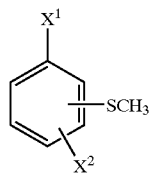
(5)

wherein $X^1$ and $X^2$ are as defined above, chlorinating the obtained methylthiohalobenzene with chlorine to obtain a chloromethylthiohalobenzene represented by the formula (6)

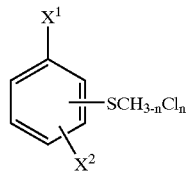
(6)

wherein $X^1$ and $X^2$ are as defined above, and n is an integer of 1 to 3, and hydrolyzing the obtained chloromethylthiohalobenzene in the presence of a lower alcohol or a base.

[Production of bishalophenyl disulfide]

In the invention, a halothiophenol of the formula (1) is reacted with an alkali metal hydroxide to give an alkali metal halothiophenolate of the formula (2).

Examples of the halogen atom represented by $X^1$ and $X^2$ in the halothiophenol of the formula (1) are Cl, Br and I among which Cl and Br are preferred. Specific examples of the halothiophenol used in the invention are 2-chlorothiophenol, 3-chlorothiophenol, 4-chlorothiophenol, 2-bromothiophenol, 3-bromothiophenol, 4-bromothiophenol, 2-iodothiophenol, 3-iodothiophenol, 4-iodothiophenol, 2,3-dichlorothiophenol, 2,4-dichlorothiophenol, 2,5-dichlorothiophenol, 3,4-dichlorothiophenol, 3,5-dichlorothiophenol, 2,3-dibromothiophenol, 2,4-dibromothiophenol, 2,5-dibromothiophenol, 3,4-dibromothiophenol, 3,5-dibromothiophenol, 2,3-diiodothiophenol, 2,4-diiodothiophenol, 2,5-diiodothiophenol, 3,4-diiodothiophenol, 3,5-diiodothiophenol, etc. Among them, it is suitable to use 2-chlorothiophenol, 3-chlorothiophenol, 4-chlorothiophenol, 2-bromothiophenol, 3-bromothiophenol, 4-bromothiophenol, 2,3-dichlorothiophenol, 2,4-dichlorothiophenol, 2,5-dichlorothiophenol, 3,4-dichlorothiophenol, 3,5-dichlorothiophenol, 2,3-dibromothiophenol, 2,4-dibromothiophenol, 2,5-dibromothiophenol, 3,4-dibromothiophenol or 3,5-dibromothiophenol.

The halothiophenol to be used in the invention is not limited to high-purity compounds. It is possible to use a halothiophenol having a purity of 30 to 97%, preferably 50 to 91%. Consequently the crude halothiophenol produced, e.g., from a halobenzene as the raw material can be used without purification.

The alkali metal hydroxide to be used in the invention is not limited and includes, for example, lithium hydroxide, potassium hydroxide, sodium hydroxide and the like. Among them, it is suitable from an economical viewpoint to use potassium hydroxide or sodium hydroxide. The amount of the alkali metal hydroxide to be used is usually 1 to 3 moles, preferably 1 to 2 moles, per mole of halothiophenol. When the alkali metal hydroxide is used in an amount of less than 1 mole, a satisfactory effect is unlikely to be achieved. On the other hand, more than 3 moles of alkali metal hydroxide used is unlikely to give the effect corresponding to the amount used and may be uneconomical. The alkali metal hydroxide is generally used in the form of an aqueous solution. Preferably the aqueous solution has a concentration of about 10 to about 40 wt %.

The temperature in the reaction between a halothiophenol and an alkali metal hydroxide is not limited, but usually −10 to 100° C., preferably 0 to 40° C. The reaction time is variable with the reaction temperature, but usually 5 minutes to 1 hour.

The alkali metal halothiophenolate resulting from the reaction between a halothiophenol and an alkali metal hydroxide is easily dissolved in an aqueous solution of alkali metal hydroxide. On the other hand, the impurities in the halothiophenol are insoluble in water. Consequently even when a low-purity halothiophenol is used as the raw material, an alkali metal halothiophenolate having a high purity can be easily recovered in the aqueous layer by separation procedure or like means after reaction. The alkali metal halothiophenolate recovered in the aqueous layer is converted in a state of aqueous solution into a disulfide using an oxidizing agent, whereby a bishalophenyl disulfide can be obtained with a high purity in a high yield.

The halothiophenol of the formula (1) is reacted with the alkali metal hydroxide to obtain an alkali metal halothiophenolate of the formula (2), and the aqueous solution of the alkali metal halothiophenolate of the formula (2) is converted into a disulfide with an oxidizing agent in the presence of a mineral acid, whereby a bishalophenyl disulfide of the formula (3) can be obtained.

Useful mineral acids are not limited and include, for example, hydrochloric acid, sulfuric acid, nitric acid, phosphoric acid, etc. Among them, it is suitable from an economical viewpoint to use hydrochloric acid. The amount of the mineral acid to be used is usually 0.01 to 1 mole per mole of halothiophenol. When the mineral acid is used in an amount of less than 0.01 mole, the reaction is likely to entail difficulty in progress. On the other hand, more than 1 mole of the mineral acid used can not give the effect corresponding to the amount used and may be uneconomical.

Useful oxidizing agents are not limited and include, for example, hydrogen peroxide, oxygen, potassium permanganate, dimethyl sulfoxide, etc. Among them, hydrogen peroxide is suitably used from an economical viewpoint. The amount of the oxidizing agent to be used is usually 0.01 to 10 moles, preferably 0.1 to 2 moles, per mole of halothiophenol. When the oxidizing agent is used in an amount of less than 0.01 mole, the yield is likely to decrease. On the other hand, more than 10 moles of the oxidizing agent used is unlikely to give the effect corresponding to the amount used and may be uneconomical.

The reaction for conversion into a disulfide can be conducted in an aqueous solution of alkali metal hydroxide or optionally using an organic solvent. Examples of useful organic solvents are hexane, cyclohexane, heptane and like hydrocarbons, dichloroethane, dichloromethane, chloroform and like halogenated hydrocarbons, benzene, toluene, xylene, monochlorobenzene, dichlorobenzene, trichlorobenzene and like aromatic hydrocarbons, methanol and like alcohols, acetone and like ketones, etc. When the organic solvent is used, the amount of the organic solvent to be used is not limited but usually 0.01 to 10 times the weight of alkali metal halothiophenolate. When the amount of the organic solvent exceeds 10 times the weight thereof, the volume efficiency is lower. Hence it is probably undesirable.

The temperature in the reaction for conversion into a disulfide is usually –10 to 100° C., preferably 0 to 50° C. When the reaction temperature is lower than –10° C., the reaction proceeds slowly and tends to take a prolonged time. On the other hand, the reaction temperature exceeding 100° C. is apt to cause a side reaction and may be responsible for reduction of yield. Hence it is probably undesirable. The reaction time is variable with the reaction temperature, but usually 0.5 to 20 hours.

The reaction for conversion into a disulfide is carried out in a homogeneous system of aqueous solution. As the reaction proceeds, the produced bishalophenyl disulfide is precipitated as a solid. Consequently the reaction is finally terminated to give a solid-liquid system. After completion of reaction, the produced bishalophenyl disulfide is separated by filtration, washed and dried, giving a high-purity bishalophenyl disulfide.

Specific examples of the thus-obtained bishalophenyl disulfide are bis(2-chlorophenyl)disulfide, bis(3-chlorophenyl)disulfide, bis(4-chlorophenyl)disulfide, bis(2-bromophenyl)disulfide, bis(3-bromophenyl)disulfide, bis(4-bromophenyl)disulfide, bis(2-iodophenyl)disulfide, bis(3-iodophenyl)disulfide, bis(4-iodophenyl)disulfide, bis(2,3-dichlorophenyl)disulfide, bis(2,4-dichlorophenyl)disulfide, bis(2,5-dichlorophenyl)disulfide, bis(3,4-dichlorophenyl)disulfide, bis(3,5-dichlorophenyl)disulfide, bis(2,3-dibromophenyl)disulfide, bis(2,4-dibromophenyl)disulfide, bis(2,5-dibromophenyl)disulfide, bis(3,4-dibromophenyl)disulfide, bis(3,5-dibromophenyl)disulfide, bis(2,3-diiodophenyl)disulfide, bis(2,4-diiodophenyl)disulfide, bis(2,5-diiodophenyl)disulfide, bis(3,4-diiodophenyl)disulfide, bis(3,5-diiodophenyl)disulfide, etc.

[Production of Halothiophenol]

The process for producing the halothiophenol to be used in the production of the bishalophenyl disulfide is not limited. According to the invention, the following process is suitably conducted. A halobenzene is reacted with sodium thiomethoxide in the presence of a quaternary phosphonium salt to obtain a methylthiohalobenzene. Subsequently the obtained methylthiohalobenzene is chlorinated with chlorine to obtain a chloromethylthiohalobenzene. The obtained chloromethylthiohalobenzene is hydrolyzed in the presence of a lower alcohol or a base.

In the process for producing the halothiophenol, a halobenzene of the formula (4) is reacted with sodium thiomethoxide (i.e., sodium methyl sulfide) in the presence of a quaternary phosphonium salt (phase transfer catalyst) to obtain a methylthiohalobenzene of the formula (5).

The halogen atom represented by $X^1$, $X^2$ and $X^3$ in the halobenzene of the formula (4) includes Cl, Br and I among which Cl and Br are preferred. Specific examples of the halobenzene to be used in the invention are 1,2-dichlorobenzene, 1,3-dichlorobenzene, 1,4-dichlorobenzene, 1,2-dibromobenzene, 1,3-dibromobenzene, 1,4-dibromobenzene, 1,2-diiodobenzene, 1,3-diiodobenzene, 1,4-diiodobenzene, 1,2,3-trichlorobenzene, 1,2,4-trichlorobenzene, 1,2,5-trichlorobenzene, 1,3,4-trichlorobenzene, 1,3,5-trichlorobenzene, 1,2,3-tribromobenzene, 1,2,4-tribromobenzene, 1,2,5-tribromobenzene, 1,3,4-tribromobenzene, 1,3,5-tribromobenzene, 1,2,3-triiodobenzene, 1,2,4-triiodobenzene, 1,2,5-triiodobenzene, 1,3,4-triiodobenzene, 1,3,5-triiodobenzene, etc. Among them, suitable to use are 1,2-dichlorobenzene, 1,3-dichlorobenzene, 1,4-dichlorobenzene, 1,2-dibromobenzene, 1,3-dibromobenzene, 1,4-dibromobenzene, 1,2,3-trichlorobenzene, 1,2,4-trichlorobenzene, 1,2,5-trichlorobenzene, 1,3,4-trichlorobenzene, 1,3,5-trichlorobenzene, 1,2,3-tribromobenzene, 1,2,4-tribromobenzene, 1,2,5-tribromobenzene, 1,3,4-tribromobenzene, 1,3,5-tribromobenzene, etc.

The amount of the sodium thiomethoxide to be used is not limited and is usually 0.1 to 3 moles, preferably 0.5 to 2 moles, per mole of halobenzene. When the sodium thiomethoxide is used in an amount of less than 0.1 mole, the reaction is liable to encounter difficulty in completion. On the other hand, more than 3 moles of sodium thiomethoxide used is unlikely to give the effect corresponding to the amount used and may be uneconomical.

Useful quaternary phosphonium salts include, for example, tetra-n-butylphosphonium bromide, hexadecyltributylphosphonium bromide, etc. Among them, tetra-n-butylphosphonium bromide is suitable to use from an economical viewpoint. The amount of the quaternary phosphonium salt to be used is not limited but usually 0.0001 to 5 moles, preferably 0.005 to 2 moles, per mole of halobenzene. When the amount is less than 0.0001 mole, the salt is unlikely to achieve the effect as a phase transfer catalyst. On the other hand, the amount exceeding 5 moles fails to perform the effect corresponding to the amount used and may be uneconomical. The quaternary phosphonium salt is used as it is or in the form of an aqueous solution. When the salt is used as an aqueous solution, the solution has a concentration of usually 10 to 60 wt %.

The quaternary phosphonium salt is separated from water after completion of the reaction, so that it can be easily recovered by separation procedure or like means. The recovered quaternary phosphonium salt can be re-used.

The reaction may be performed with or without a solvent, or using a halobenzene itself as the solvent. Useful solvents are not limited and include, for example, hexane, cyclohexane, heptane and like hydrocarbons, dichloroethane, trichloroethane and like halogenated hydrocarbons, benzene, toluene, xylene, monochlorobenzene, dichlorobenzene, trichlorobenzene and like aromatic hydrocarbons. When the solvent is used in the reaction, the amount of the solvent to be used is not limited but usually 0.01 to 10 times the weight of halobenzene. When the amount of the solvent exceeds 10 times the weight of halobenzene, the volume efficiency is lower. Hence it is probably undesirable.

The temperature in the foregoing reaction is usually 30 to 200° C., preferably 50 to 150° C. When the reaction temperature is lower than 30° C., the reaction proceeds slowly and tends to take a prolonged time. On the other hand, the reaction temperature exceeding 200° C. is apt to cause a side reaction and may be responsible for reduction of yield. Hence it is presumably undesirable. The reaction time is variable with the reaction temperature, but usually 1 to 30 hours, preferably 3 to 10 hours.

Subsequently the methylthiohalobenzene of the formula (5) prepared by the foregoing reaction is chlorinated with chlorine to give a chloromethylthiohalobenzene of the formula (6).

The amount of the chlorine to be used is usually 1 to 10 moles, preferably 2 to 3 moles, per mole of methylthiohalobenzene. When the chlorine is used in an amount of less than 1 mole, the reaction is liable to encounter difficulty in completion, whereas more than 10 moles of chlorine used is unlikely to give the effect corresponding to the amount used and may be uneconomical.

The reaction for chlorination can be conducted with or without a solvent. Examples of the solvent are hexane, cyclohexane, heptane and like hydrocarbons, dichloroethane, dichloromethane, chloroform and like halogenated hydrocarbons, benzene, toluene, xylene, monochlorobenzene, dichlorobenzene, trichlorobenzene and like aromatic hydrocarbons, etc. When the solvent is used, the amount of the solvent to be used is usually 0.1 to 10 times the weight of metylthiohalobenzene. When the amount of the solvent exceeds 10 times the weight thereof, the volume efficiency is lower. Hence it may be probably undesirable.

The temperature in the chlorination reaction is usually 0 to 120° C., preferably 20 to 80° C. When the reaction temperature is lower than 0° C., the reaction proceeds slowly and tends to take a prolonged time. On the other hand, the reaction temperature exceeding 120° C. is apt to cause a side reaction and may be responsible for reduction of yield. Hence it is probably undesirable. The reaction time is variable with the reaction temperature but is usually 0.5 to 20 hours.

The thus-obtained chloromethylthiohalobenzene can be isolated from the reaction mixture by conventional distillation or crystallization. Optionally the reaction mixture may be used in hydrolysis without isolation.

The chloromethylthiohalobenzene of the formula (6) prepared by the foregoing process is hydrolyzed in the presence of a lower alcohol or a base, whereby a halothiophenol of the formula (1) can be produced.

Useful lower alcohols are methanol, ethanol, isopropanol, n-propanol, isobutanol, n-butanol, sec-butanol, etc. Among them, methanol is suitable to use from an economical viewpoint. The amount of the lower alcohol to be used is usually 0.5 to 10 times the weight of chloromethylthiohalobenzene. When the lower alcohol is used in an amount of less than 0.5 times the weight thereof, the reaction is liable to encounter difficulty in completion, whereas more than 10 times is unlikely to give the effect corresponding to the amount used and may be uneconomical.

Useful bases to be used are not limited and include, for example, sodium hydroxide, sodium carbonate, sodium hydrogencarbonate and like inorganic bases, dimethylamine, triethylamine and like amines, N,N-dimethylformamide, N-methylpyrrolidone and like amides, pyridine, etc. Among them, dimethylamine, triethylamine and like amines, N,N-dimethylformamide, N-methylpyrrolidone and like amides, etc. are suitable to use. The amount of the base to be used is usually 0.01 to 1 times the weight of chloromethylthiohalobenzene. The amount of less than 0.01 times the weight thereof is likely to encounter difficulty in completing the reaction, whereas more than 1 times is unlikely to give the effect corresponding to the amount used and may be uneconomical.

The hydrolysis reaction can be carried out with or without a solvent. Useful solvents are not limited and include, for example, hexane, cyclohexane, heptane and like hydrocarbons, dichloroethane, dichloromethane, chloroform and like halogenated hydrocarbons, benzene, toluene, xylene, monochlorobenzene, dichlorobenzene, trichlorobenzene and like aromatic hydrocarbons, etc. When the solvent is used, the amount of the solvent to be used is usually 0.1 to 10 times the weight of chloromethylthiohalobenzene. When the amount of the solvent exceeds 10 times the weight thereof, the volume efficiency is lower. Hence it is probably undesirable.

It is possible to conduct the reaction with one pot using the same solvent as used in the chlorination reaction.

The temperature in the hydrolysis reaction is usually 30 to 200° C., preferably 60 to 110° C. When the reaction temperature is lower than 30C.°, the reaction proceeds slowly and tends to take a prolonged time. On the other hand, the reaction temperature exceeding 200° C. is apt to cause a side reaction and may be responsible for reduction of yield. Hence it is probably undesirable. The reaction time is variable with the reaction temperature, but usually 0.5 to 20 hours.

A bishalophenyl disulfide which is used for a wide variety of applications including medicine, agricultural chemicals, functional materials and the like can be industrially produced with a high purity in a high yield.

BEST MODE FOR CARRYING OUT THE INVENTION

The present invention will be described in more detail with reference to the following examples to which, however, the invention is not limited.

EXAMPLE 1

A 4-necked, 1-liter flask equipped with a stirrer, a thermometer and a condenser tube was charged with 181.5 g (1.00 mole) of 1,3,5-trichlorobenzene and 67.9 g (0.10 mole) of an aqueous solution of 50 wt % tetra-n-butylphosphonium bromide. 233.6 g (1.00 mole) of an aqueous solution of 30 wt % sodium thiomethoxide was added dropwise at 80° C. over a period of 6 hours. After addition, the mixture was reacted at the same temperature for 10 hours. After completion of reaction, 191.9 g of a crude 1-methylthio-3,5-dichlorobenzene was obtained by separation procedure.

99.4 g (1.40 moles) of chlorine was blown into the obtained crude 1-methylthio-3,5-dichlorobenzene at 50° C. over a period of 8 hours to carry out chlorination reaction at the same temperature for 1 hour. Then, 120 g of N,N-dimethylformamide and 240 g of water were added for hydrolysis reaction at 100° C. for 3 hours.

After completion of reaction, the mixture was subjected to separation procedure at 60° C., giving 163.1 g of crude 3,5-dichlorothiophenol (purity 90.4%). The obtained crude 3,5-dichlorothiophenol contained 147.5 g (0.824 mole) of 3,5-dichlorothiophenol, which was produced in a yield of 82.4% based on 1,3,5-trichlorobenzene.

EXAMPLE 2

A 4-necked, 1-liter flask equipped with a stirrer, a thermometer and a condenser tube was charged with 147.0 g (1.00 mole) of 1,4-dichlorobenzene and 67.9 g (0.10 mole) of an aqueous solution of 50 wt % tetra-n-butylphosphonium bromide. 233.6 g (1.00 mole) of an aqueous solution of 30 wt % sodium thiomethoxide was added dropwise at 80° C. over a period of 6 hours. After addition, the mixture was reacted at the same temperature for 10 hours. After completion of reaction, 157.4 g of a crude 1-methylthio-4-chlorobenzene was obtained by separation procedure.

150 g of monochlorobenzene was added to the obtained crude 1-methylthio-4-chlorobenzene. 134.9 g (1.9 moles) of chlorine was blown into the mixture at 50° C. over a period of 3 hours. Then, chlorination reaction was performed at the same temperature for 1 hour. 240 g of methanol and 50 g of water were added. Then hydrolysis reaction was carried out at 70° C. for 5 hours.

After completion of reaction, 500 g of water was added to the reaction mixture. Thereafter the mixture was subjected to separation procedure, giving a solution of 4-chlorothiophenol (impurities 13.3%) in monochlorobenzene. The obtained solution contained 125.9 g (0.871 mole) of 4-chlorothiophenol. The yield was 87.1% based on 1,4-dichlorobenzene.

EXAMPLE 3

A 4-necked, 1-liter flask equipped with a stirrer, a thermometer, a dropping funnel and a condenser tube was charged with 163.1 g (0.824 mole of 3,5-dichlorothiophenol) of the crude 3,5-dichlorothiophenol (purity 90.4%) prepared by the process of Example 1, and 370 g (0.925 mole) of an aqueous solution of 10 wt % sodium hydroxide. After 15 minutes of reaction at 25° C., the reaction mixture was subjected to separation procedure to give an aqueous solution of sodium 3,5-dichlorothiophenolate.

50 g (0.479 mole) of an aqueous solution of 35 wt % hydrochloric acid was added to the obtained aqueous solution and 49.5 g (0.51 mole) of an aqueous solution of 35 wt % hydrogen peroxide was added dropwise at 20° C. over a period of 1 hour. After completion of dropwise addition, the mixture was reacted for 1 hour.

After completion of reaction, the crystals were separated by filtration, washed and dried, giving 141.2 g (0.396 mole) of bis(3,5-dichlorophenyl)disulfide. The obtained bis(3,5-dichlorophenyl)disulfide had a purity of 99.9% as determined by high performance liquid chromatography. The disulfide was prepared in a yield of 96.1% based on 3,5-dichlorothiophenol.

EXAMPLE 4

A 4-necked, 1-liter flask equipped with a stirrer, a thermometer, a dropping funnel and a condenser tube was charged with a monochlorobenzene solution (0.871 mole of 4-chlorothiophenol) of 4-chlorothiophenol (13.3% of impurities) prepared by the process of Example 2 and 520 g (0.929 mole) of an aqueous solution of 10 wt % potassium hydroxide. The mixture was reacted at 25° C. for 15 minutes and was subjected to separation procedure to give an aqueous solution of potassium 4-chlorothiophenolate.

50 g (0.479 mole) of an aqueous solution of 35 wt % of hydrochloric acid was added to the obtained aqueous solution and 51.5 g (0.53 mole) of an aqueous solution of 35 wt % hydrogen peroxide was added dropwise at 20° C. over a period of 1 hour. After completion of dropwise addition, the mixture was reacted for 1 hour.

After completion of reaction, the crystals were separated by filtration, washed and dried, giving 120.1 g (0.418 mole) of bis(4-chlorophenyl)disulfide. The obtained bis(4-chlorophenyl)disulfide had a purity of 99.9% as determined by high performance liquid chromatography. The disulfide was prepared in a yield of 96.0% based on 4-chlorothiophenol.

COMPARATIVE EXAMPLE 1

A 4-necked, 1-liter flask equipped with a stirrer, a thermometer, a dropping funnel and a condenser tube was charged with 163.1 g (0.824 mole of 3,5-dichlorothiophenol) of the crude 3,5-dichlorothiophenol (purity 90.4%) prepared by the process of Example 1 and 300 g of methanol. Then, 49.5 g (0.51 mole) of an aqueous solution of 35 wt % hydrogen peroxide was added dropwise at 20° C. over a period of 1 hour. After completion of dropwise addition, the mixture was reacted for 1 hour.

After completion of reaction, the mixture was crystallized at 5° C. and crystals were separated by filtration, washed and dried, giving 156.1 g (0.395 mole) of bis(3,5-dichlorophenyl)disulfide. The obtained bis(3,5-dichlorophenyl)disulfide had a purity of 90.1% as determined by a high performance liquid chromatography. The disulfide was produced in a yield of 95.9% based on 3,5-dichlorothiophenol.

What is claimed is:

1. A process for producing a bishalophenyl disulfide represented by the formula (3)

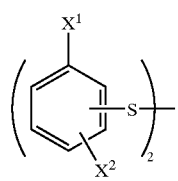
(3)

wherein $X^1$ is a halogen atom and $X^2$ is a halogen atom or a hydrogen atom, the process comprising the steps of reacting a halothiophenol represented by the formula (1)

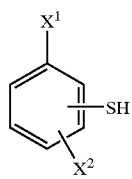
(1)

wherein $X^1$ and $X^2$ are as defined above with an alkali metal hydroxide to obtain an alkali metal halothiophenolate represented by the formula (2)

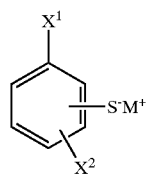
(2)

wherein $X^1$ and $X^2$ are as defined above, and M is an alkali metal atom and subsequently converting the alkali metal halothiophenolate into a disulfide with an oxidizing agent in the presence of a mineral acid.

2. The process according to claim 1, wherein the alkali metal hydroxide is potassium hydroxide or sodium hydroxide.

3. The process according to claim 1, wherein the mineral acid is hydrochloric acid.

4. The process according to claim 1, wherein the oxidizing agent is hydrogen peroxide.

5. The process according to claim 1, wherein the halothiophenol is 2-chlorothiophenol, 3-chlorothiophenol, 4-chlorothiophenol, 2-bromothiophenol, 3-bromothiophenol, 4-bromothiophenol, 2,3-dichlorothiophenol, 2,4-dichlorothiophenol, 2,5-dichlorothiophenol, 3,4-dichlorothiophenol, 3,5-dichlorothiophenol, 2,3-dibromothiophenol, 2,4-dibromothiophenol, 2,5-dibromothiophenol, 3,4-dibromothiophenol or 3,5-dibromothiophenol.

6. The process according to claim 1, wherein the halothiophenol of the formula (1) is prepared by the steps of reacting a halobenzene represented by the formula (4)

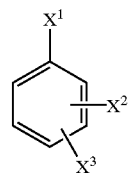
(4)

wherein $X^1$ and $X^3$ are each a halogen atom and $X^2$ is a halogen atom or a hydrogen atom, with sodium thiomethoxide in the presence of a quaternary phosphonium salt to obtain a methylthiohalobenzene represented by the formula (5)

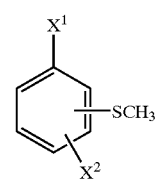
(5)

wherein $X^1$ and $X^2$ are as defined above, chlorinating the obtained methylthiohalobenzene with chlorine to obtain a chloromethylthiohalobenzene represented by the formula (6)

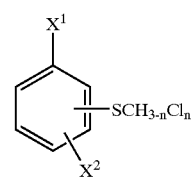
(6)

wherein $X^1$ and $X^2$ are as defined above, and n is an integer of 1 to 3, and hydrolyzing the obtained chloromethylthiohalobenzene in the presence of a lower alcohol or a base.

7. A process for producing a halothiophenol represented by the formula (1)

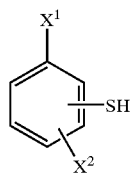
(1)

wherein $X^1$ is a halogen atom and $X^2$ is a halogen atom or a hydrogen atom, the process comprising the steps of reacting a halobenzene represented by the formula (4)

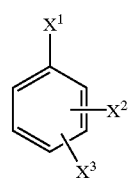
(4)

wherein $X^1$ and $X^2$ are as defined above, and $X^3$ is a halogen atom, with sodium thiomethoxide in the presence of a quaternary phosphonium salt to obtain a methylthiohalobenzene represented by the formula (5)

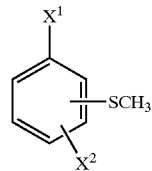

(5)

wherein $X^1$ and $X^2$ are as defined above, chlorinating the obtained methylthiohalobenzene with chlorine to obtain a chloromethylthiohalobenzene represented by the formula (6)

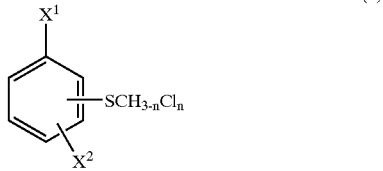

(6)

wherein $X^1$ and $X^2$ are as defined above, and n is an integer of 1 to 3, and hydrolyzing the obtained chloromethylthiohalobenzene in the presence of a lower alcohol or a base.

* * * * *